United States Patent
Bai et al.

(10) Patent No.: US 11,242,326 B2
(45) Date of Patent: Feb. 8, 2022

(54) MULTIVALENT LIGAND FOR MYOTONIC DYSTROPHY

(71) Applicant: The Board of Trustees of the University of Illinois, Urbana, IL (US)

(72) Inventors: Yugang Bai, Changsha (CN); Steven C. Zimmerman, Champaign, IL (US); Auinash Kalsotra, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 52 days.

(21) Appl. No.: 16/641,450

(22) PCT Filed: Aug. 23, 2018

(86) PCT No.: PCT/US2018/047756
§ 371 (c)(1),
(2) Date: Feb. 24, 2020

(87) PCT Pub. No.: WO2019/040750
PCT Pub. Date: Feb. 28, 2019

(65) Prior Publication Data
US 2020/0399231 A1    Dec. 24, 2020

Related U.S. Application Data

(60) Provisional application No. 62/577,946, filed on Oct. 27, 2017, provisional application No. 62/550,299, filed on Aug. 25, 2017.

(51) Int. Cl.
| | | |
|---|---|---|
| *C07D 251/64* | (2006.01) | |
| *A61K 9/00* | (2006.01) | |
| *A61K 9/06* | (2006.01) | |
| *A61K 9/20* | (2006.01) | |
| *A61K 9/48* | (2006.01) | |

(52) U.S. Cl.
CPC .......... *C07D 251/64* (2013.01); *A61K 9/0019* (2013.01); *A61K 9/06* (2013.01); *A61K 9/2054* (2013.01); *A61K 9/2059* (2013.01); *A61K 9/4858* (2013.01)

(58) Field of Classification Search
CPC .............................. C07D 251/54; A61K 31/53
See application file for complete search history.

(56) References Cited

U.S. PATENT DOCUMENTS

| | | |
|---|---|---|
| 5,834,451 A | 11/1998 | Ohsawa et al. |
| 6,987,123 B2 | 1/2006 | Lohray et al. |
| 7,589,123 B2 | 9/2009 | Rees et al. |
| 7,704,951 B2 | 4/2010 | Hirashima et al. |
| 8,754,084 B2 | 6/2014 | Zimmerman et al. |
| 9,376,421 B2 | 6/2016 | Zimmerman et al. |
| 9,382,215 B2 | 7/2016 | Zimmerman et al. |
| 10,266,520 B2 | 4/2019 | Zimmerman et al. |
| 2005/0004125 A1 | 1/2005 | Freyne et al. |
| 2008/0227213 A1 | 9/2008 | Disney |
| 2010/0323993 A1 | 12/2010 | Berglund et al. |

FOREIGN PATENT DOCUMENTS

WO    2016023039 A1    2/2016

OTHER PUBLICATIONS

Arambula et al., "A Simple Ligand that Selectively Targets CUG Trinucleotide Repeats and Inhibits MBNL Protein Binding," Proc Natl Acad Sci U S A, 106(38):16068-16073, Sep. 2009.
Bai et al., "Integrating Display and Delivery Functionality with a Cell Penetrating Peptide Mimic as a Scaffold for Intracellular Multivalent Multitargeting," J. Am. Chem. Soc., 138(30):9498-9507, Jun. 2016.
David, et al., "DNA Mismatch-Specific Base Flipping by a Bisacridine Macrocycle," Chembiochem, 4(12):1326-1331, Dec. 2003.
Gareiss, et al., "Dynamic Combinatorial Selection of Molecules Capable of Inhibiting the (CUG) Repeat RNA-MBNL 1 Interaction In Vitro: Discovery of Lead Compounds Targeting Myotonic Dystrophy (DM1)," J Am Chem Soc, 130(48):16254-16261, Dec. 2008.
International Search Report and Written Opinion of the ISA/US in International Application No. PCT/US2015/044526 dated Nov. 19, 2015; 8pgs.
International Search Report and Written Opinion of the ISA/US in International Application No. PCT/US2018/047756, dated Oct. 11, 2018; 6pgs.
Jahromi et al., "A Novel CUGexp•MBNL1 Inhibitor with Therapeutic Potential for Myotonic Dystrophy Type 1," ACS Chem. Biol., 8(5):1037-1043, Mar. 2013.
Jahromi et al., "Developing Bivalent Ligands to Target CUG Triplet Repeats, the Causative Agent of Myotonic Dystrophy Type 1," J. Med. Chem., 56(23):9471-9481, Nov. 2013.
Jahromi et al., "Rational Design of Potent Dimeric Ligands as Potential Theraputic Agents for Myotonic Dystrophy Type I (DM1)," Biophys J., 102(3):483A, Jan. 2012.
Jahromi, A.H., et al., "Single-molecule Study of the CUG Repeat-MBNL1 Interaction and Its Inhibition by Small Molecules," Nucleic Acids Res., 41(13):6687-6697, Jul. 2014.
Jiang et al., "Myotonic Dystrophy Type 1 is Associated with Nuclear Foci of Mutant RNA, Sequestration of Muscleblind Proteins and Deregulated Alternative Splicing in Neurons," Hum Mol Genet., 13(24):3079-3088, Dec. 2004.

(Continued)

Primary Examiner — Deepak R Rao
(74) Attorney, Agent, or Firm — Haukaas Fortius PLLC; Michael H. Haukaas

(57) ABSTRACT

Abnormally long r(CUG)n repeat expansion is believed to be the major cause of Myotonic dystrophy type 1 (DM1) because it binds to muscleblind-like 1 (MBNL 1) protein which regulates RNA splicing, leading to the mis-splicing of more than 100 pre-mRNAs. The rational design of oligomers with alternating bisamidine and melamine structure resulted in good binding affinity to the RNA target because of a multivalent effect. The oligomers also showed excellent activity in disrupting nuclear foci, reversing the mis-splicing of IR minigene, and sabotaging the toxic RNA biosynthesis. Excellent activity in *Drosophila* based DM1 models was also observed for the oligomers, rescuing the climbing ability of the flies upon oral treatment.

18 Claims, 12 Drawing Sheets

(56) References Cited

OTHER PUBLICATIONS

Kiessling et al., "Synthetic Multivalent Ligands in the Exploration of Cell-Surface Interactions," Curr Opin Chem Biol., 4(6):696-703, Dec. 2000.
Lee et al., "Intrinsically Cell-Penetrating Multivalent and Multi-Targeting Ligands for Myotonic Dystrophy Type," PNAS, 116(18):8709-8714, Apr. 2019.
Luu et al., "A Potent Inhibitor of Protein Sequestration by Expanded Triplet (CUG) Repeats that Shows Phenotypic Improvements in a *Drosophila* Model of Myotonic Dystrophy," ChemMedChem. 11(13):1428-1435, Jul. 2016.
Mooers, et al., "The Structural Basis of Myotonic Dystrophy from the Crystal Structure of CUG Repeats," Proc Natl Acad Sci U S A., 102(46):16626-16631, Nov. 2005.
Nguyen et al., "Rationally Designed Small Molecules that Target Both the DNA and RNA Causing Myotonic Dystrophy Type 1," J Am Chem Soc., 137(44):14180-14189, Nov. 2015.
Nguyen et al., "Small Molecules that Target the Toxic RNA in Myotonic Dystrophy Type 2," ChemMedChem., 9(11):2455-2462, Nov. 2014.
Wong et al., "Targeting Toxic RNAs that Cause Myotonic Dystrophy Type 1 (DM1) with a Bisamidinium Inhibitor," J. Am. Chem. Soc., 136(17):6355-6361, Apr. 2014.
Wong, C.H., "Discovery of Small Molecule Inhibitors of MBNL • RNA Interaction: Toward Therapeutic Agents to Treat Myotonic Dystrophy," The Chinese University of Hong Kong, Jan. 2012. 9pgs.
Wong, et al., "Selective Inhibition of MBNL1-CCUG Interaction by Small Molecules Toward Potential Therapeutic Agents for Myotonic Dystrophy Type 2 (DM2)," Nucleic Acids Res, 39(20):8881-8890, Nov. 2011.

- ⊘ U-U INTERACTING WITH THE LIGAND
- ○ U-U NOT INTERACTING WITH THE LIGAND
- ● LIGAND

ENLARGED H-BONDING ILLUSTRATIONS
LIGAND & BINDING MOTIFS: C N O P H

ENLARGED H-BONDING ILLUSTRATIONS
LIGAND & BINDING MOTIFS: C N O P H

ENLARGED H-BONDING ILLUSTRATIONS
LIGAND & BINDING MOTIFS: C N O P H

Mice fed with Dox 6g/kg)　　Daily injections and continued Dox diet　IP injections end Day 0　　1　　　　　　　　　　　　　　　　　　　　　　　　7　　8

IP injections started
Experimental group with Oligomer (2mg/kg)
Control group with water Mice sacrificed Oligomer Treated Mice　　　　　　　　　ApoE -Dox ApoE960 +Dox and water

MULTIVALENT LIGAND FOR MYOTONIC DYSTROPHY

RELATED APPLICATIONS

This application is a National Stage filing under 35 U.S.C. § 371 of International Application No. PCT/US2018/047756 filed Aug. 23, 2018, which claims priority under 35 U.S.C. § 119(e) to U.S. Provisional Patent Applications Nos. 62/550,299, filed Aug. 25, 2017, and 62/577,946, filed Oct. 27, 2017 which are incorporated herein by reference.

GOVERNMENT SUPPORT

This invention was made with government support under Grant No. R01 AR069645 awarded by the National Institutes of Health. The government has certain rights in the invention.

BACKGROUND OF THE INVENTION

Multivalencey is an established and effective strategy for the development of potent, selective-binding ligands. The advantage of multivalent ligands arises from the thermodynamic and kinetic advantages of the properly-aligned multiple copies of receptor-binding moieties over their monomer analogue, via different mechanisms such as steric stabilization, receptor clustering, chelate effect, and concentration effect. The improvements in ligand affinity and selectivity toward its target rely much on the alignment of ligand copies, and a "fit" is usually necessary for maximizing the multivalent effect. For example, dimeric ligand can be viewed as an extremely simplified version of multivalent ligand, and fine tuning on the linkage between two binding motifs is typically necessary even in this simplified situation. Most commonly, ligands can be post-installed onto a polymer or a surface, which usually gives statistical distribution of the ligands on their vectors. Although the construction of multivalent ligands usually grants huge benefits, even if the linkage and topology between the binding moieties are not intentionally adjusted, fine adjustments to the way of ligand assembly is an attractive approach for multivalent ligands of higher activity.

Myotonic dystrophy type 1 (DM1) is one of the many incurable trinucleotide repeat expansion diseases (TREDS). An RNA gain-of-function model for DM1 involves the rCUG$^{exp}$ transcript binding and sequestering a protein named muscleblind-like 1 (MBNL1), which is the key splicing regulator involved in the splicing of many pre-mRNAs.

Accordingly, there is a need for a small molecule approach to alleviate the sequestration of MBNL1 and the symptoms that arise from DM1.

SUMMARY

One strategy for DM1 treatment is to selectively inhibit the transcription of CTG$^{exp}$ that forms the toxic CUG$^{exp}$ or bind CUG$^{exp}$ so that the MBNL sequestration can be relieved or eliminated (FIG. 1). Considering the regular and repetitive nature of the target DNA or RNA expansions, this strategy is well suited to a multivalent approach for the search of more potent and selective ligand. Alternatively, or simultaneously another strategy involves inhibiting the sequestration of MBNL proteins by CUG$^{exp}$.

Accordingly, this disclosure provides a multivalent ligand comprising Formula I:

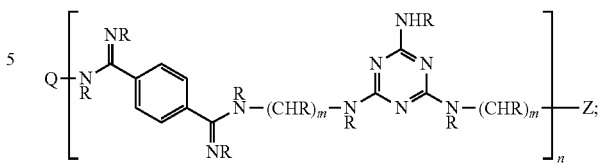

or a salt thereof;
  wherein
  Q and Z are terminal ends of Formula I;
  each R is independently H or branched or unbranched —(C$_1$-C$_6$)alkyl;
  m is 2-8; and
  n is 2-20.

Additionally, this disclosure provides a method of preparing a multivalent ligand disclosed above, comprising:
  a) contacting a mixture of a dialkyl terephthalimidate and an (aminoalkyl)triaminotriazine to form a product; and
  b) acidifying the product;
wherein the acidified product provides the multivalent ligand above.

Also, this disclosure provides a method of relieving a sequestered muscleblind-like 1 (MBNL1) protein, comprising contacting a sequestered MBNL1 protein with the multivalent ligand above or a pharmaceutical composition thereof, wherein the sequestered MBNL1 protein is sequestered by rCUG(exp), and the multivalent ligand selectively binds to one or more CUG moieties of rCUG(exp), thereby relieving the sequestered MBNL1 protein.

The invention provides novel compounds of Formula I, intermediates for the synthesis of compounds of Formula I, as well as methods of preparing compounds of Formula I and II. The invention also provides compounds of Formula I that are useful as intermediates for the synthesis of other useful compounds. The invention provides for the use of compounds of Formula I for the manufacture of medicaments useful for the treatment of myotonic dystrophy in a mammal, such as a human.

The invention provides for the use of the compositions described herein for use in medical therapy. The medical therapy can be treating myotonic dystrophy type 1. The invention also provides for the use of a composition as described herein for the manufacture of a medicament to treat a disease in a mammal, for example, myotonic dystrophy type-1, in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
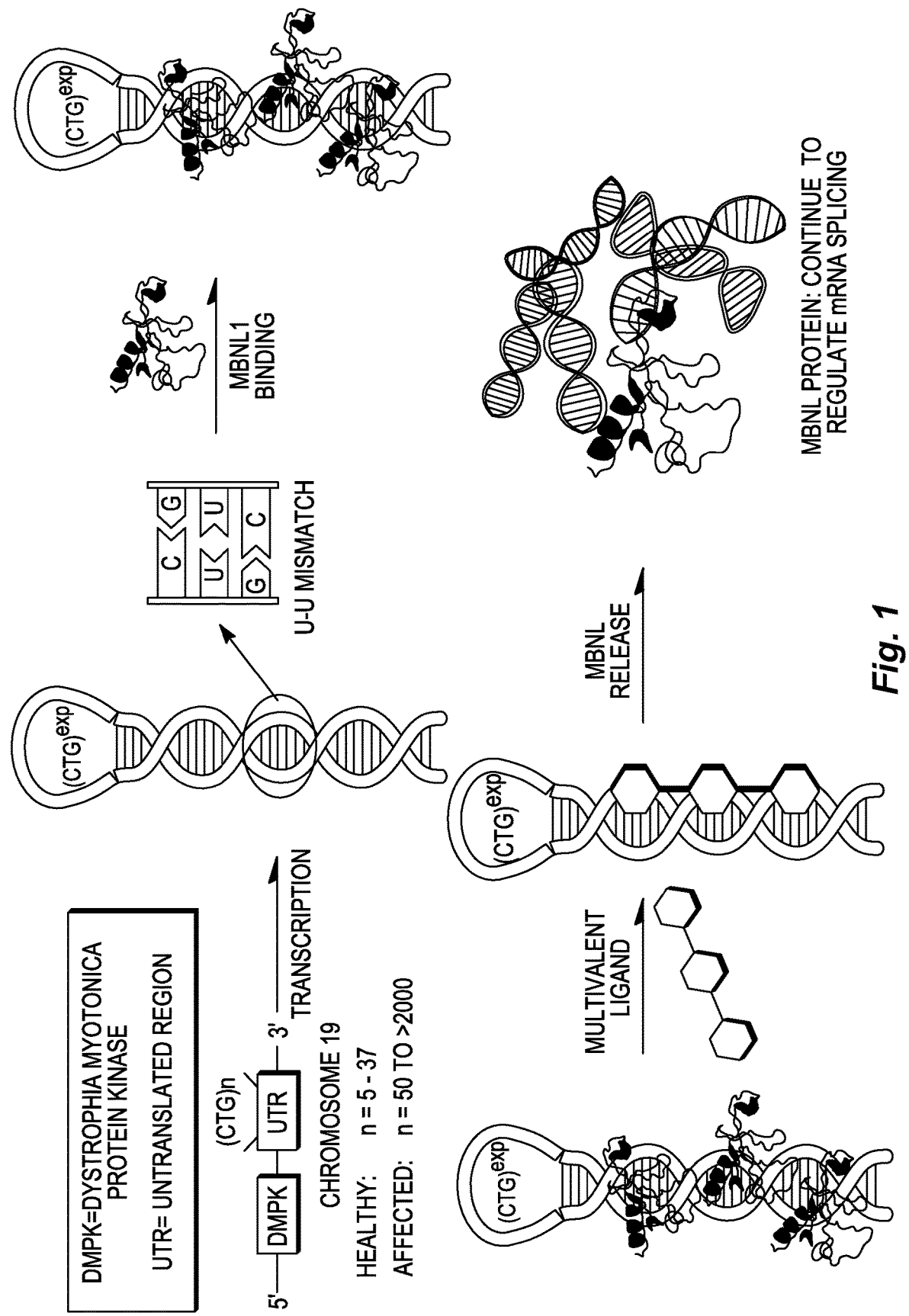
FIG. 1. Illustration of RNA gain-of-function mechanism leading to MBNL sequestration and DM1 symptoms, and the multivalent approach for re-activating MBNL by using ligands targeting rCUG$^{exp}$.

Abnormally long r(CUG)n repeat expansion is believed to be the major cause of Myotonic dystrophy type 1 (DM1) because it binds to muscleblind-like 1 (MBNL1) protein which regulates RNA splicing, leading to the mis-splicing of more than 100 pre-mRNAs. A rational design of a bisamidine-based small molecule ligand that selectively binds to $CUG^{exp}$ has been previously reported. Utilizing its groove-binding mode and optimized structure of this ligand, facile chemistry was used to synthesize oligomers with alternating bisamidine and melamine structure which have much higher binding strength to the RNA target compared to the original ligand because of the multivalent effect.

The present disclosure provides for the first time a one-step synthesis of a multivalent ligand targeting $rCUG^{exp}$, with rationally designed linker length between the recognition moieties. The strategy does not involve the incorporation of ligand moieties on any kind of vectors. Instead, the vector is the oligomer itself, a direct assembly of the binding moieties, without any redundant framework structures. This ligand has significantly improved efficacy in a DM1 cell model, showing low nanomolar Ki against r(CUG)n-MBNL1 interaction, capability of dispersing ribonuclear foci and high splicing rescue of insulin receptor (IR) pre-mRNA at low concentrations. The oligomer ligand was also tested in vivo using a DM1 *Drosophila* climbing assay, and significant phenotypic improvement on the flies after ligand feeding was observed.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four substituents on the phenyl ring.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art.

However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term, "repeat unit", "repeating unit", or "block" as used herein refers to the moiety of a polymer that is repetitive. The repeat unit may comprise one or more repeat units, labeled as, for example, repeat unit A, repeat unit B, repeat unit C, etc. Repeat units A-C, for example, may be covalently bound together to form a combined repeat unit. Monomers or a combination of one or more different monomers can be combined to form a (combined) repeat unit of a polymer or copolymer.

The term "molecular weight" for the copolymers disclosed herein refers to the average number molecular weight (Mn). The corresponding weight average molecular weight (Mw) can be determined by a calculation known to the skilled artisan.

The term "copolymer" refers to random or block copolymers, as shown by the "r" (for random) or "b" (for block) in a Formula In various embodiments, the terminal ends of a polymer or oligomer, is a low molecular weight moiety (e.g. under 500 Da), such as, H, OH, OOH, $CH_2OH$, CN, $NH_2$, or a hydrocarbon, such as but not limited to, an alkyl (for example, a butyl or 2-cyanoprop-2-yl moiety), alkene or alkyne, or a moiety as a result of an elimination reaction at the first and/or last repeat unit in a polymer.

Embodiments of the Invention

This disclosure provides various embodiments of a multivalent ligand comprising Formula I:

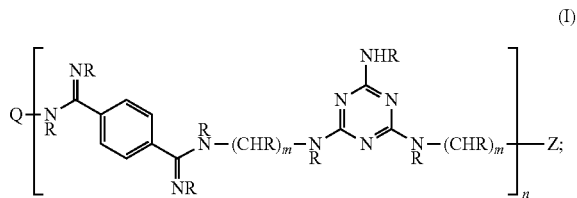

(I)

or a salt thereof;

wherein

Q and Z are terminal ends of Formula I;

each R is independently H or branched or unbranched —$(C_1-C_6)$alkyl;

m is 2-8; and n is 2-20.

In some embodiments, m is 2-20. In other embodiments, n is 1-100. In further embodiments, Z is H, OR, $NR_2$, or Formula IB:

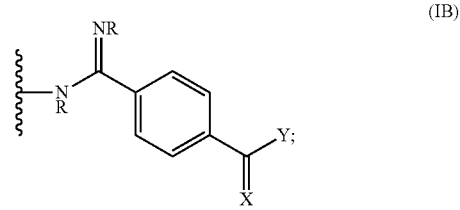

(IB)

wherein X is O or NR; and Y is OR or $NR_2$.

In yet other embodiments, Q is H or —$(CHR)_n$-$G^1$, wherein $G^1$ is H, OR, $NR_2$, or Formula IC:

(IC)

[Structure IC: triazine with NHR group, flanked by two N-R groups, one connected to J, other to wavy bond]

wherein J is H or —(CHR)$_n$-G$^2$, and G$^2$ is H, OR, NR$_2$, or Formula IB.

In additional embodiments, R is H. In other embodiments, m is 4. In yet other embodiments n is 2-5, or n is 4-8. In further embodiments, the molecular weight of the multivalent ligand is about 0.5 kDa to about 10 kDa, about 1 kDa to about 5 kDa, or is less than 100 kDa. In yet other embodiments, the molecular weight is about 1500 amu to about 3500 amu (data from mass spectral analysis shows peaks at 1586 to 3393 which corresponds to 4-mers to 8-mers, e.g., in Formula I, n is about 4 to about 8).

In various other embodiments, the multivalent ligand selectively binds to rCUG(exp). In yet other embodiments, the multivalent ligand has a binding affinity (Ki) of about 1 nanomolar to about 10 micromolar, or less than 100 micromolar.

In some additional embodiments, the multivalent ligand is cell permeable. In various other embodiments, the multivalent ligand relieves a sequestered muscleblind-like 1 (MBNL1) protein, wherein the sequestered MBNL1 protein is sequestered by rCUG(exp). In yet other embodiments, the multivalent ligand inhibits transcription of CTG(exp).

In one aspect, the present disclosure provides a composition comprising the following structures:

This disclosure also provides a pharmaceutical composition comprising the multivalent ligand disclosed above in combination with a pharmaceutically acceptable diluent, carrier, excipient, or buffer.

Additionally, this disclosure also provides a method of preparing a multivalent ligand disclosed above, comprising:
 a) contacting a mixture of a dialkyl terephthalimidate and an (aminoalkyl)triaminotriazine to form a product; and
 b) acidifying the product;
wherein the acidified product provides the multivalent ligand above.

In yet other additional embodiments, dialyzing the acidified product forms a purified product.

This disclosure also provides a method of relieving a sequestered muscleblind-like 1 (MBNL1) protein, comprising contacting a sequestered MBNL1 protein with a multivalent ligand disclosed above (or a pharmaceutical composition thereof), wherein the sequestered MBNL1 protein is sequestered by rCUG(exp), and the multivalent ligand selectively binds to one or more CUG moieties of rCUG(exp), thereby relieving the sequestered MBNL1 protein.

Additionally, this disclosure provides a method of reducing the symptoms of myotonic dystrophy type 1 (DM1) comprising administering to a subject having DM1 an effective amount of a multivalent ligand disclosed above, thereby reducing the symptoms of DM1. In other additional embodiments, the multivalent ligand selectively binds to one or more CUG moieties of rCUG(exp).

In other embodiments, the symptoms of DM1 reduced by the administration of an effective amount of a multivalent ligand (or composition thereof) are one or more of myopathy, myotonia, progressive muscle atrophy, cataracts, cardiac defect, and insulin dependent diabetes. In yet other embodiments, the area of a focal inclusion in a nucleus is reduced in a cell afflicted with DM1. In further embodiments, the effective amount is a concentration of about 0.1 micromolar to about 10 micromolar.

[Chemical structures labeled •2A, •3A, •4A depicting multivalent ligand polymers with triazine, aminoalkyl, and benzamidinium units]

wherein
 n=1-20;
 R=H or ethyl; and
 A=Cl$^-$, Br$^-$, I$^-$, TFA$^-$, HSO$_4^-$, AcO$^-$, HCO$_3^-$, TsO$^-$, MsO$^-$, or PhSO$_3^-$.

In additional embodiments, contacting a sequestered MBNL1 protein with a multivalent ligand is in a cell afflicted with myotonic dystrophy type 1 (DM1), and the area of a focal inclusion in the nucleus of the cell is reduced compared to the area of a focal inclusion in the nucleus of a second cell afflicted with DM1, when a sequestered MBNL1 protein is not in contact with the multivalent ligand in the second cell.

This disclosure additionally provides a multivalent ligand disclosed above for use in the treatment of myotonic dystrophy type 1 (DM1) in a subject afflicted with DM1, wherein a therapeutically effective amount of the multivalent ligand is administered to the subject. In some embodiments, mis-splicing of the insulin receptor pre-mRNA minigene is reversed.

In another aspect, the present disclosure provides a method of selectively inhibiting CTG(exp) in a subject, the method comprising administering a subject a therapeutically effective amount of the compositions disclosed herein.

In yet another aspect, the present disclosure also provides a method of treating myotonic dystrophy type I in a subject, the method comprising administering a subject a therapeutically effective amount of the compositions disclosed herein.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion Section

The strategy for the disclosed ligands had used a precisely controlled multivalent display of bonding interactions through a fixed linker length between the recognition moieties adopted from a previously characterized small molecule ligand. The rational design of the oligomer was based on the structural feature of the small molecule ligand and the RNA target, as well as the known groove-binding model. The design allows easy, one-step synthesis of an oligomeric construct with enhanced nucleotide binding capacity, water solubility and cell permeability. The designed oligomer had shown excellent activity in both in vitro and in vivo assays, with good toxicity profile in DM1 patient cells, DM1 *Drosophila* and mice (MTD=40 mg/kg).

In a broader perspective, although the exact structural design may not be easily adopted for other known agents for DM1, it again showed the usefulness of a multivalent design and illustrated an important design philosophy, that generating a cell-permeable, multivalent ligand based on known binding moieties can be an efficient and powerful way to improve binding strength as well as selectivity, and potentially the efficacy of therapeutics operating intracellularly. This design philosophy is likely to be viable for other ligands developed for TREDS diseases considering the similarity in pathogenesis of DM1 and other TREDS.

Abnormally long r(CUG)n repeat expansion is believed to be the major cause of Myotonic dystrophy type 1 (DM1) because it binds to muscleblind-like 1 (MBNL 1) protein which regulates RNA splicing, leading to the missplicing of more than 100 pre-mRNAs. A rational design of a bisamidine-based small molecule ligand that selectively binds to $CUG^{exp}$ was previously reported. Utilizing its groove-binding mode and optimized structure of this ligand, facile chemistry was used to synthesize oligomers with alternating bisamidine and melamine structure. These oligomers were directly assembled from the binding motifs without the need of using a vector and had much higher binding strength to the RNA target compared to the original ligand because of the multivalent effect. The oligomers also showed excellent activity in disrupting nuclear foci, reversing the missplicing of IR minigene, and sabotaging the toxic RNA biosynthesis. Excellent activity in *Drosophila* based DM1 models was also observed for the oligomers, rescuing the climbing ability of the flies upon oral treatment.

Rational Design of the Inhibitor

Figure 2:
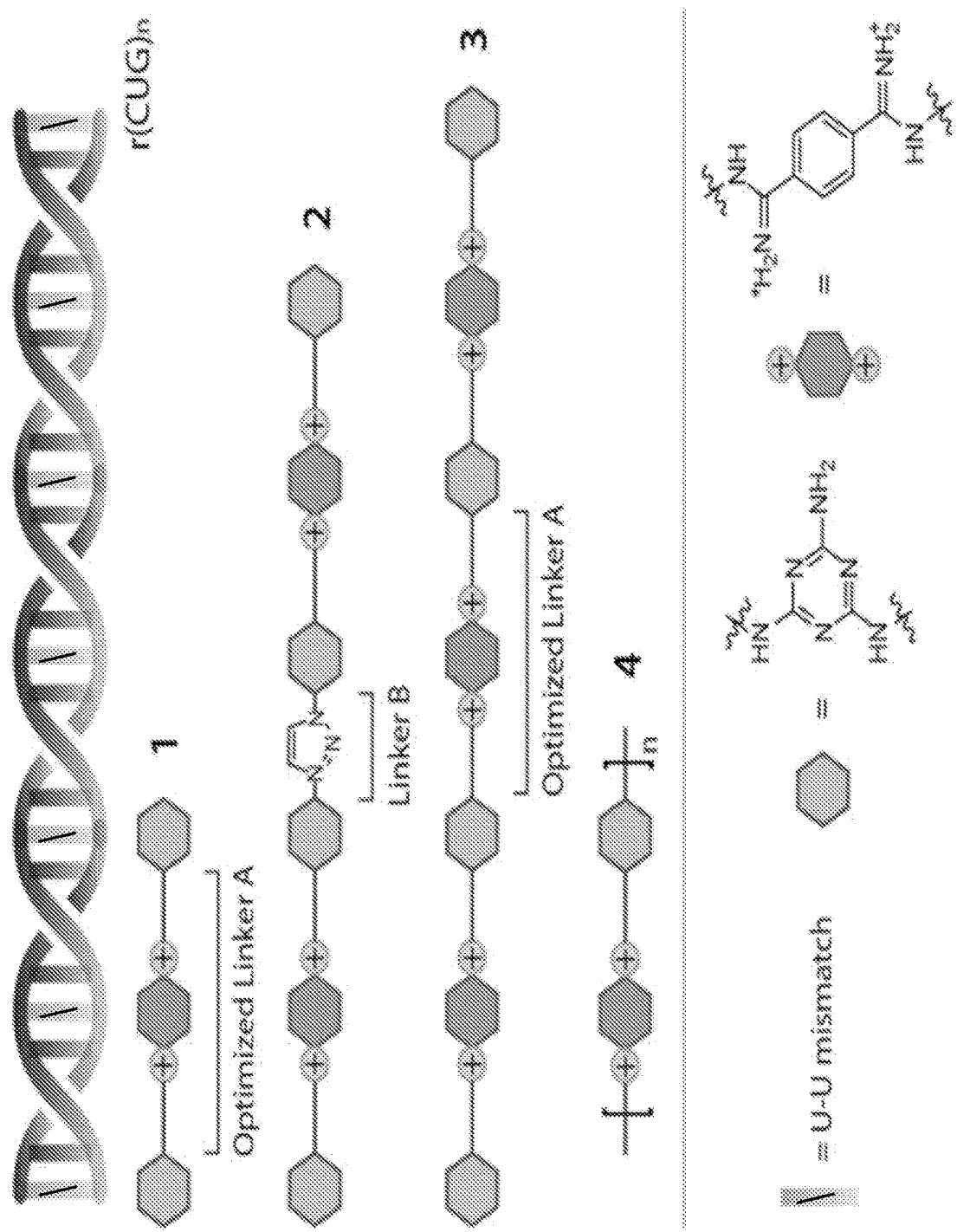
FIG. 2. Rational design of the multivalent oligomer 4 from the known bisamidine ligand 1.

A small molecule inhibitor of r(CUG)n-MBNL1 interaction was reposted (*J. Am. Chem. Soc.* 2014, 136, 6355), which contains two of triaminotriazine recognition units and a terephthalamidine core and acts as a groove binder, selectively recognizing two of every three U-U mismatches on the folded target RNA (1 in FIG. 2). The length of the linker connecting the triaminotriazine and the core was modified, which had a significant effect on the binding strength. In addition, similar to a previous approach for the acridine-based inhibitor, 1 was dimerized to give 2 with a triazole linker between two monomeric units, which greatly improved its performance in cellular and *Drosophila* DM1 models. However, the dimer synthesis required much more time and efforts due to the multi-step route to the asymmetric triaminotriazine moieties, and the optimization of the linker length between the two monomeric units calls for even more synthetic efforts.

With careful observation, one can easily recognize that 1 actually of dimeric essence, with optimized linker length between the triaminotriazine and terephthalamidine units, allowing the matching of the first and third U-U mismatches in three consequent CUG repeats. This means that a linker with four methylene groups and a terephthalamidine moiety gives the optimized distance between the two triaminotriazine units, yet this important information was not utilized in the dimer synthesis because a triazole was mandatorily placed on the linker, which requires additional tuning on its length. However, a possible alternative design is to use the same linker within 1, connecting the monomeric units with another set of one terephthalamidine and two —($CH_2$)$_4$— chains. This approach apparently yields a more structurally regular 3, hopefully with no further need for the optimization of the linker length because it was already optimized when designing 1. The additional terephthalamidine in 3 also provides extra groove-binding scaffold for CUG recognition, potentially helping the selectivity and affinity. Furthermore, based on the regularly repetitive structure of 3, it can be further elongated in the same fashion, giving oligomeric or even polymeric 4 with multivalent binding capability. Considering the polycationic nature, pre-optimized and regularly arrayed binding moieties, as well as the ease in synthesis of 4, this rationally designed oligomerization strategy suggested a good potential in the improvement of the known monomeric ligand.

Molecular Modelling Study

Figure 3:
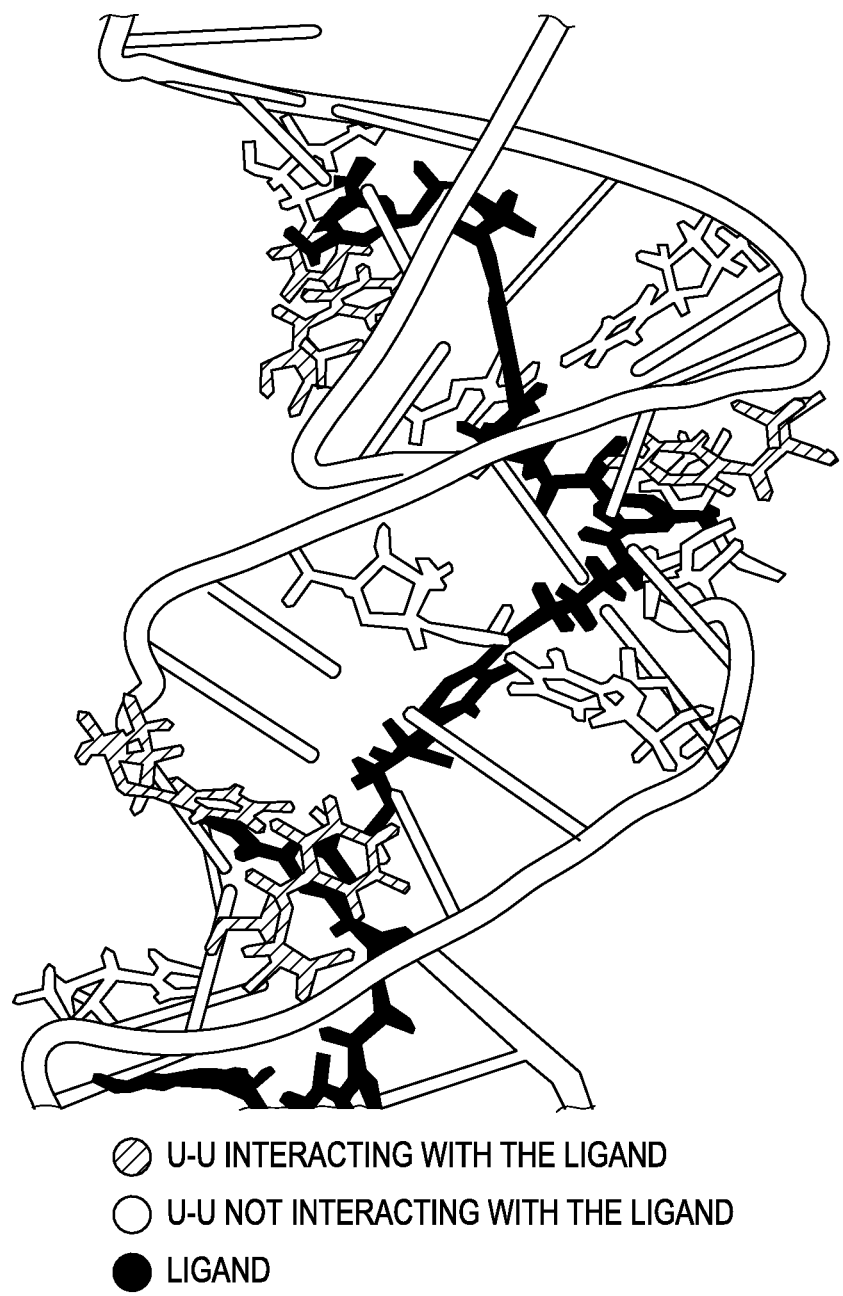
FIG. 3. Molecular modelling of ligand 4 (DP=3.5) with [r(CUG)15]2 repeats. MD simulations showed that 4 binds to the rCUG duplex in the major groove, recognizing the U-U mismatches through hydrogen bonding with triaminotriazine moieties.
Figure 3:
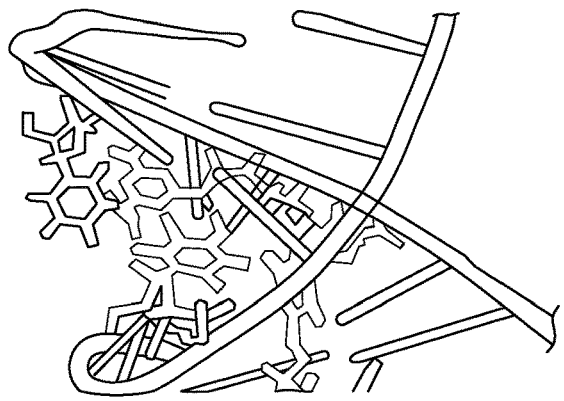
Figure 3:
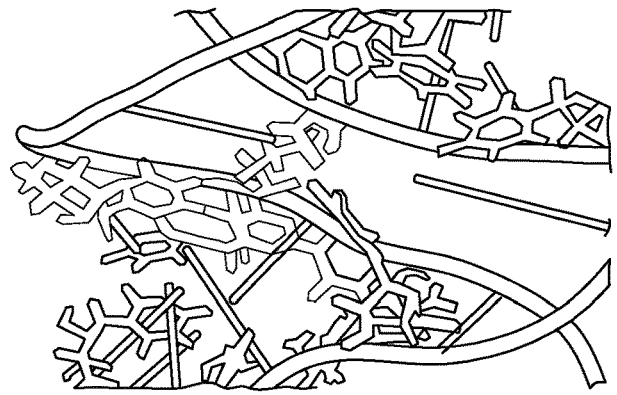
Figure 3:
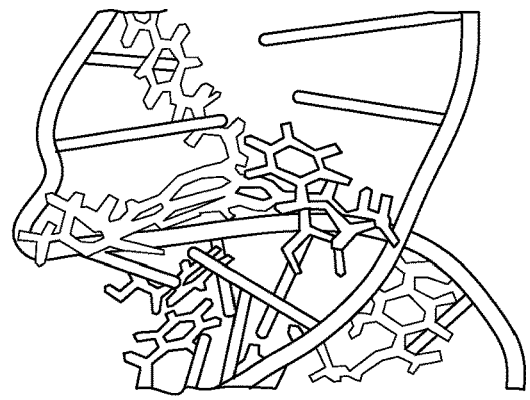
Figure 4:
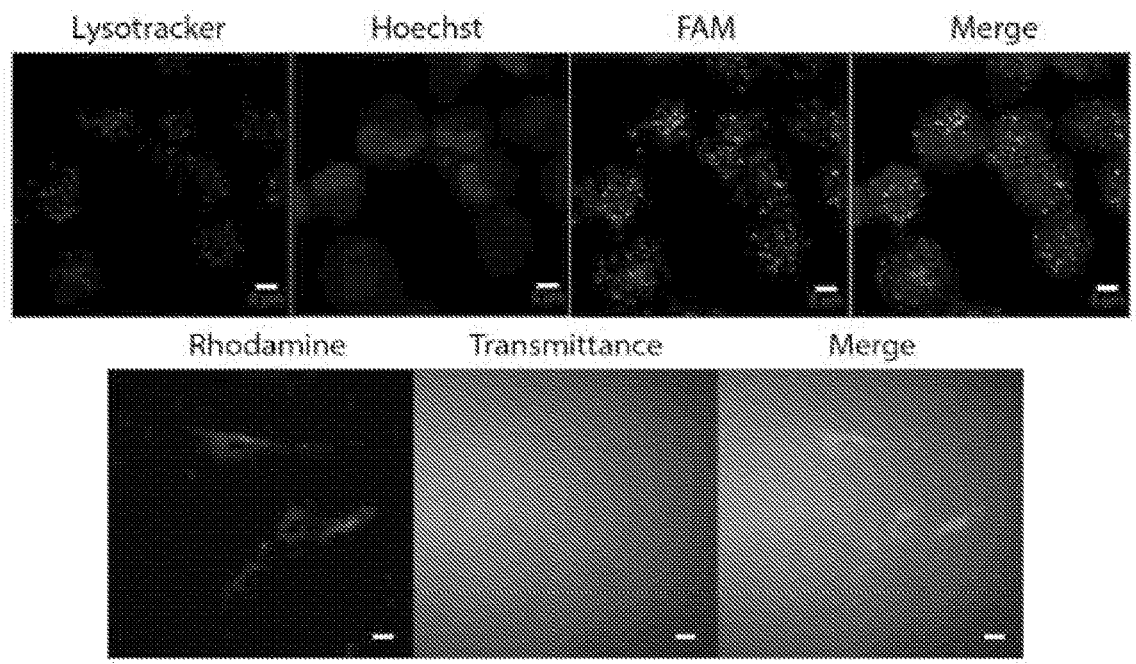
FIG. 4. HeLa (top) and DM1 myoblast (bottom) cellular uptake study using confocal microscopy. The oligomeric ligand 4 was labelled using fluorescein isothiocyanate or Rhodamine B isothiocyanate, and Lysotracker Red was used to study the uptake mechanism. For HeLa cell, [4]=1 μM, incubation time=4 h. For DM1 myoblast, [4]=2 μM, incubation time=24 h. Scale bar=5 μm.

To validate the disclosed molecular design, a molecular modelling study using MD simulations was performed using a strategy similar to a previous report on the monomeric ligand 1. By manually docking the oligomeric ligand 4 (DP=3.5, with three bisamidinium moieties and four triaminotriazine units) into [r(CUG)15]2 based on the MD simulation result of ligand 1, a 10 ns MD simulation suggested stable major group binding with the triaminotriazine units recognizing every other U-U mismatches in a row (FIG. 3).

The recognized uracil rings were on the same planes of the triaminotriazine units, forming multiple hydrogen bonds. This computational study further supports the rational design of the oligomeric ligand, and the designed ligand 4 was thus synthesized for in vivo and in vitro studies.

Polycondensation Strategy for Oligomerization

The reaction between primary amine and ethyl imidate are generally clean addition-elimination reactions similar to many esterification and amidation reactions. However, since aromatic imidates are weaker electrophiles compared to aliphatic imidates because of the conjugation to the neighbouring π-system, terephthalimidate used in this reaction is of relatively low reactivity towards the amine. Therefore, the polycondensation between the two monomers reliably yields low molecular weight (MW) oligomeric products at slightly elevated temperature (35° C.). Controlling the degree of polymerization (DP) is important, as the MW greatly affects the product's cell penetration capability and cytotoxicity. Because the product's charge density is irrelevant to its chain length, its cell permeability usually goes down as MW increases because of the size effect. On the contrary, polycationic macromolecules generally have higher cytotoxicity for higher MW, because of its greater capability of membrane disruption and non-specific binding. In addition, aromatic amino groups on the triaminotriazines are poor nucleophiles, which ensures the absence of cross-linking at lower temperature. In sum, by limiting the degree of polymerization utilizing imidates' chemical reactivity, as well as the removal of smaller conjugates via dialysis, desired oligomeric products were obtained with an average MW of ca. 2 kDa (DP 5).

Improved r(CUG)n Binding Affinity by Oligomerization

The binding affinity of ligand 4 toward r(CUG) was studied using isothermal titration calorimetry (ITC). Because of the multivalency of both the ligand 4 and the RNA, the binding between the two is much more complicated compared to the monomeric ligand 1. The U-shaped curve is similar to the observation made on the dimeric ligand 2, suggesting a positively cooperative binding event. The exact binding constant or the structure of the bound complex are unknown, although dynamic light scattering (DLS) studies suggest larger polyplex formation with increased concentration of ligand 4. For the binding between 4 and RNA, the heat generated was much higher, indicating a greater enthalpy advantage for the multivalent binding. The curve also has sharp transitions, possibly suggests a tight binding between the two. The binding of 4 and a random-sequence dsDNA, on the contrary to r(CUG), is unfavored in enthalpy.

Oligomeric Ligand 4 is Cell Permeable

Figure 5:
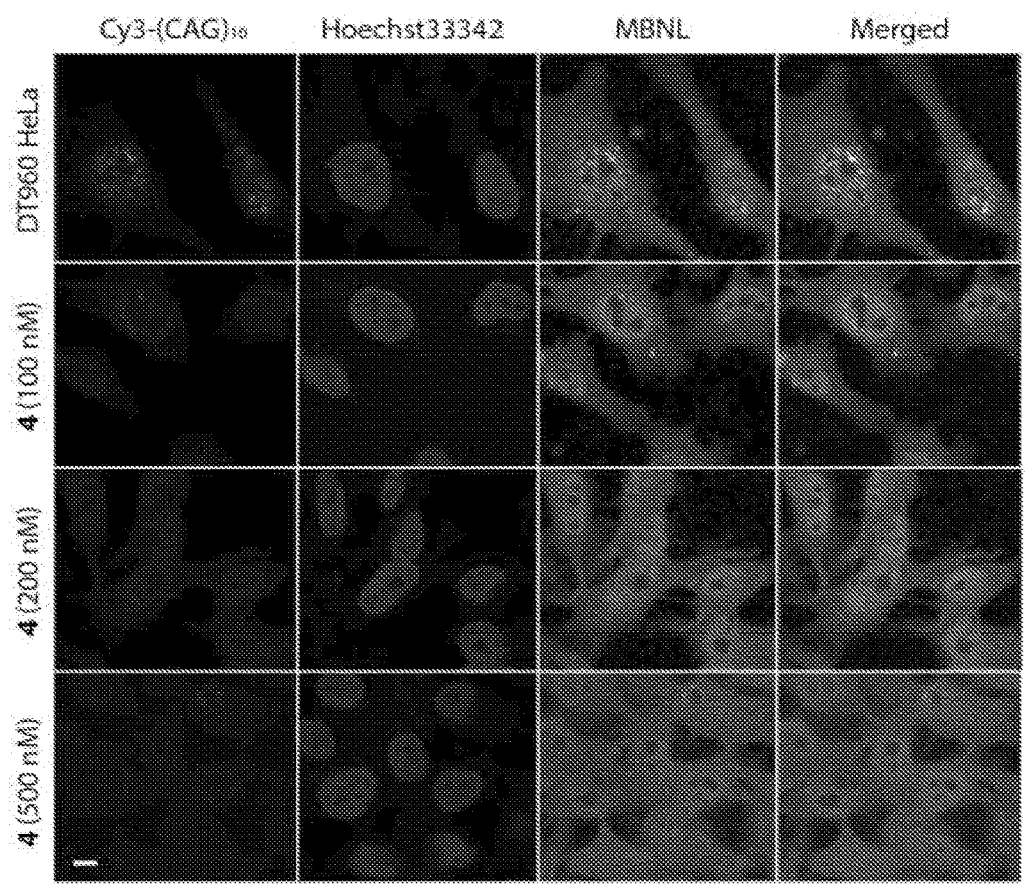
FIG. 5. Significant reduction of nuclear foci in the HeLa-based DM1 model cells were observed by treating the cells with oligomeric ligand 4 (100 nM to 500 nM) for 48 h. Higher concentration of 4 resulted in more reduction of total foci area in cells. Scale bar=5 μM.

A typical concern about macromolecular ligands has been their ability to enter the cells because of their larger size. To investigate the cell permeability of oligomer 4, which is the other important factor in addition to the binding affinity, confocal microscopy was used to visualize the oligomers inside the model cells. The oligomer was fluorescently labelled by attaching fluorescein (FAM) or Rhodamine B (RhB) using isothiocyanate-amine conjugation chemistry, and was incubated with two different model cells, HeLa cells and Human DM1 myoblasts. For both cell lines, fluorescence could be observed inside the cell, confirming the cell permeability of the oligomer 4 (FIG. 5). Also, Lysotracker Red was used to study the mechanism of the cell penetration. From the image it can be seen that the fluorescence from Lysotracker Red does not fully overlap with FAM fluorescence from the ligand, suggesting that active penetration is an important cell uptake pathway for 4, in addition to endocytosis. In sum, by using a polycationic structure, oligomer 4 showed no compromise in cell permeability, which had been an important part of the rational design of this oligomeric ligand.

Oligomer 4 Significantly Reduces Ribonuclear Foci in a DM1 Cell Model

Figure 6:
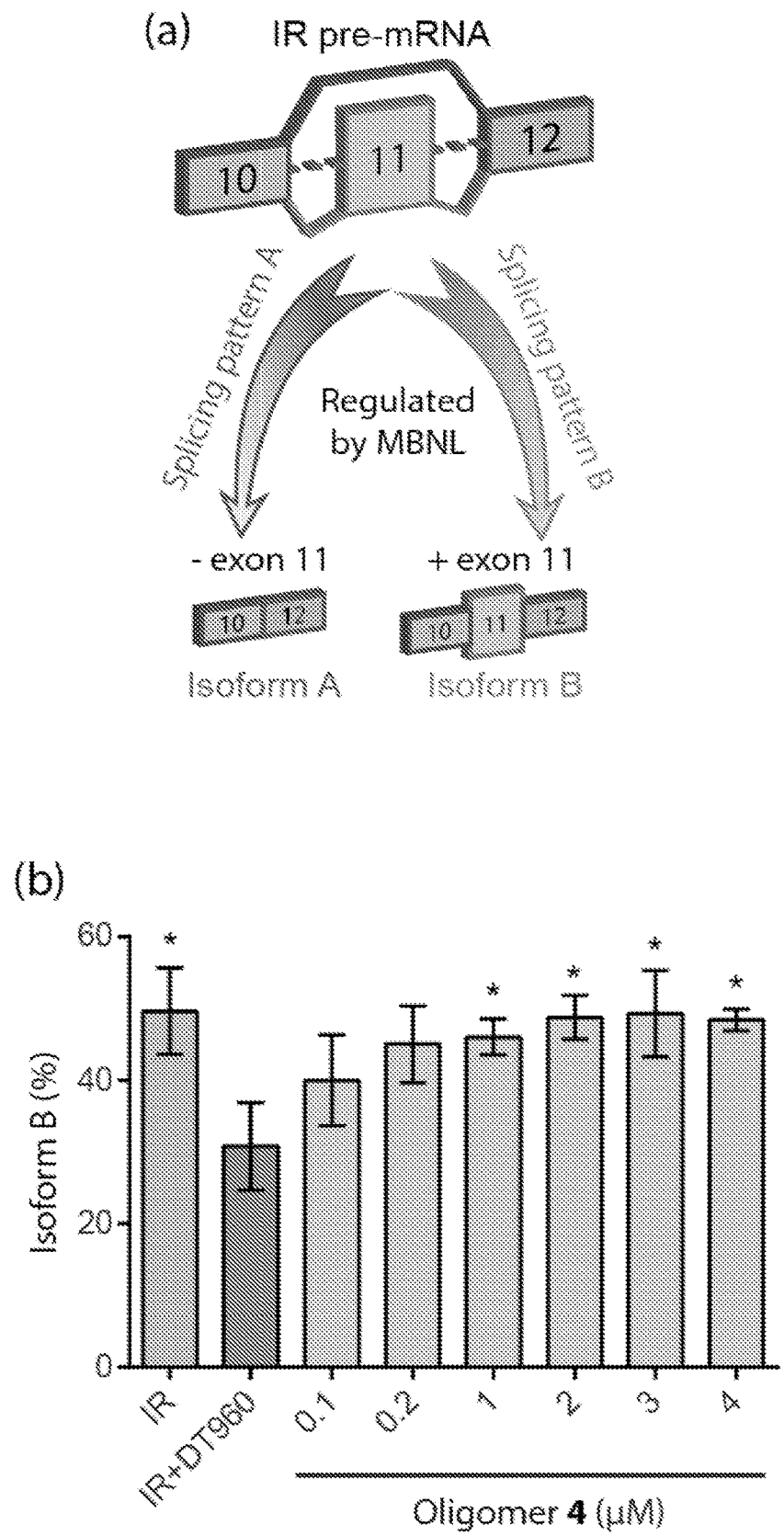
FIG. 6. (a) Cartoon illustration of IR pre-mRNA splicing regulated by MBNL protein. (b) Treatment of DM1 model cells with 4 for 72 h resulted in significant rescue of the mis-splicing of the two IR mRNA isoforms.

The formation of nuclear foci is one of the hallmarks of cells affected by DM1, which is resulted from MBNL sequestration by $CUG^{exp}$. By using a complimentary DNA strands with fluorescence tag, Cy3-(CAG), these foci can be readily visualized by confocal microscopy. Similar to previous reports, the HeLa-based DM1 model cells were constructed by transfecting the cells with a GFP-DT960 plasmids containing (CTG)960 in a truncated DMPK gene and a sequence encoding GFP protein to assess the transfection efficiency. As seen in FIG. 6, in the untreated "diseased" cells, the co-localization of Cy3-(CAG) and an anti-MBNL antibody led to the visualization of nuclear foci (FIG. 6, row 1). In contrast, cells treated with 4 of various concentrations for 48 h had showed fewer foci with noticeably smaller size (FIG. 6, row 2-4). Statistical analysis had shown that the reduction in foci area upon oligomer 4 treatment was significant, although the dose-dependence of the reduction was small in the 100-500 nM concentration window. In addition, the working concentration of the oligomer was more than three orders of magnitude lower than that of the small molecule ligand 1 (100 μM), showing a significant improvement in efficacy for this rationally designed multivalent ligand system.

Oligomer 4 Rescues the Mis-Splicing of IR Pre-mRNA in a DM1 Cell Model

Oligomer 4 was shown to inhibit foci formation and sequestration of MBNL1 by binding $rCUG^{exp}$. Since the direct downstream effect of MBNL1 sequestration is the mis-regulation of pre-mRNAs, a study was performed to determine if the mis-splicing could be rescued by 4. DM1 model cells were used, constructed by co-transfecting HeLa cells with plasmids containing DT960 and the IR minigene, which was chosen for study because it is relatively difficult to be rescued. As seen in FIG. 6a, the IR pre-mRNA can undergo two possible splicing pathways, and two isoforms, A and B, were regulated by controlling the inclusion of exon 11.

The DM1 model cells were treated with 4 at various concentrations (1-4 μM). The ratios of two IR isoforms were measured for treated and untreated cells. The splicing of IR pre-mRNA in HeLa cells containing the IR but not the DT960 minigene (e.g. "healthy" cells) produced ca. 50% of isoform B (with exon 11 inclusion), whereas only ca. 31% of isoform B was observed for the HeLa cells containing both IR and DT960 minigenes (e.g. "diseased" cells). Such differences in the IR splicing pattern generally reproduces the observation in normal and DM1 patient cells. Treatment of the "diseased" cells with 4 started to show significant rescue of the splicing defect of IR pre-mRNA starting from 1 μM (FIG. 6b), and almost fully reversed splicing pattern could be observed for the cells treated with 1-4 μM of 4. Under conditions similar to those used in the testing of small molecule ligands 1, which showed only partial rescue even at much higher concentrations (100 μM), significantly higher activity was observed for 4, presumably from its higher binding affinity and cell permeability. Importantly, at the working concentration range, 4 showed no sign of cytotoxicity toward different cell lines including patient-derived DM1 fibroblasts GM03987.

Oligomer 4 Suppress Cellular Levels of CUG$^{exp}$ RNA Transcript

It is already known that the CUG$^{exp}$ can produce additional toxicity beyond the MBNL sequestration, which adds more complexity towards DM1 disease pathobiology. For example, the CUG$^{exp}$ transcript can disrupt the translation of MEF2 protein and lead to microRNA dysregulation in DM1 heart tissue. It is also found that CUG$^{exp}$ can involve in repeat-associated non-ATG (RAN) translation, resulting in homo-peptides that may be toxic. For these reasons, the focus has been on ligands that not only bind CUG$^{exp}$, but also reduce the level of CUG$^{exp}$ inside cells. Small molecules and peptide-based polymers that target DM1 simultaneously through multiple pathways were previously reported. In this work, the potential of oligomer 4 in regulating the cellular level of CUG$^{exp}$ using a similar strategy was examined.

Figure 7:
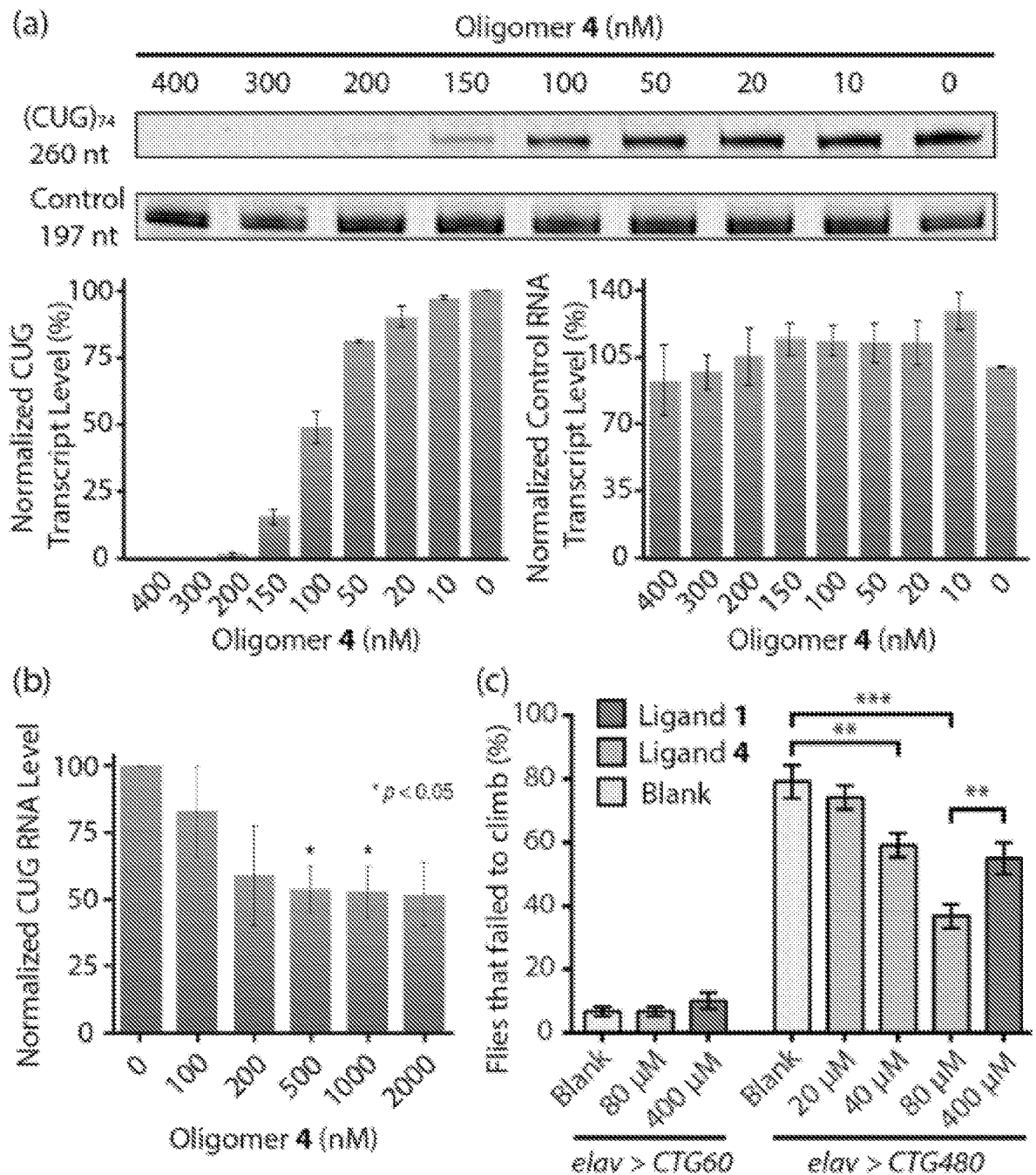
FIG. 7. (a) In vitro transcription inhibition study using a linearized plasmid containing (CTG.CAG)74 and control plasmids in presence of oligomer 4. The results clearly indicate the strong and selective inhibition on CUG transcription by low concentration of 4. (b) Significant mRNA level reduction was observed in model HeLa cells treated by 4. (c) Results from the climbing assay using DM1 *Drosophila* model and 4. Monomeric ligand 1 was also studied for comparison. N=3, n=40 individual flies.
Figure 8:
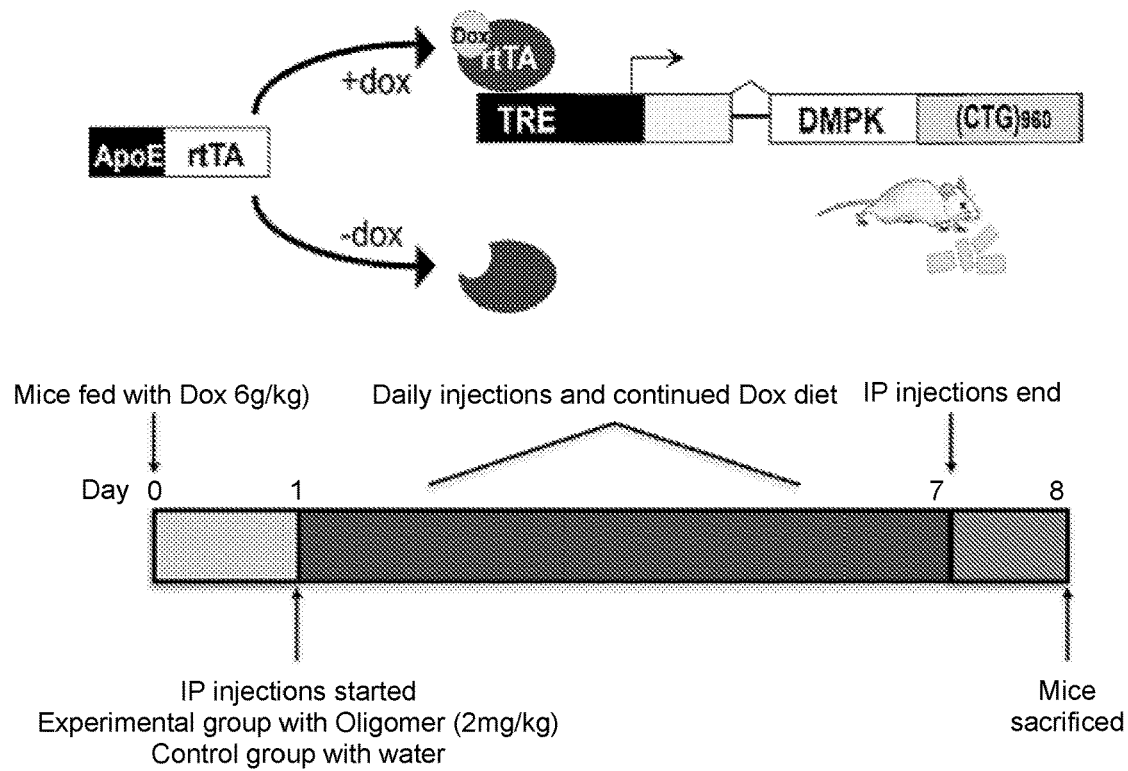
FIG. 8. Myotonic Dystrophy Type 1 Liver Model.
Figure 9:
FIG. 9. Liver Samples of Mice Treated with Butyl-linked Oligomer.
Figure 9:
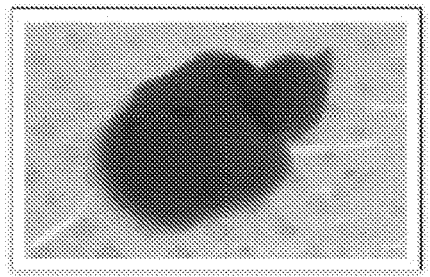
Figure 9:
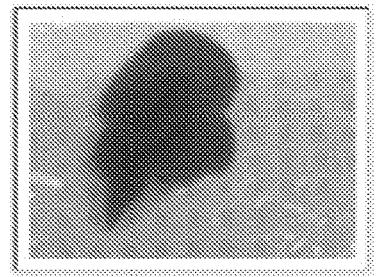
Figure 9:
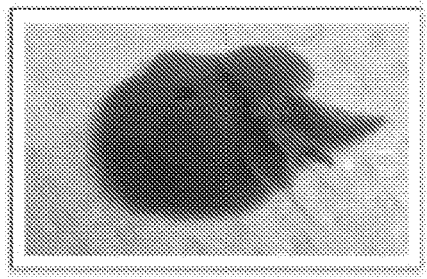
Figure 9:
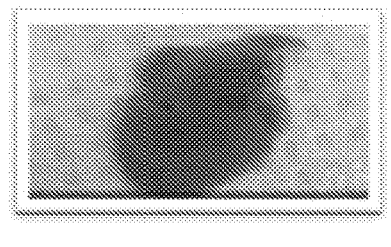
Figure 10:
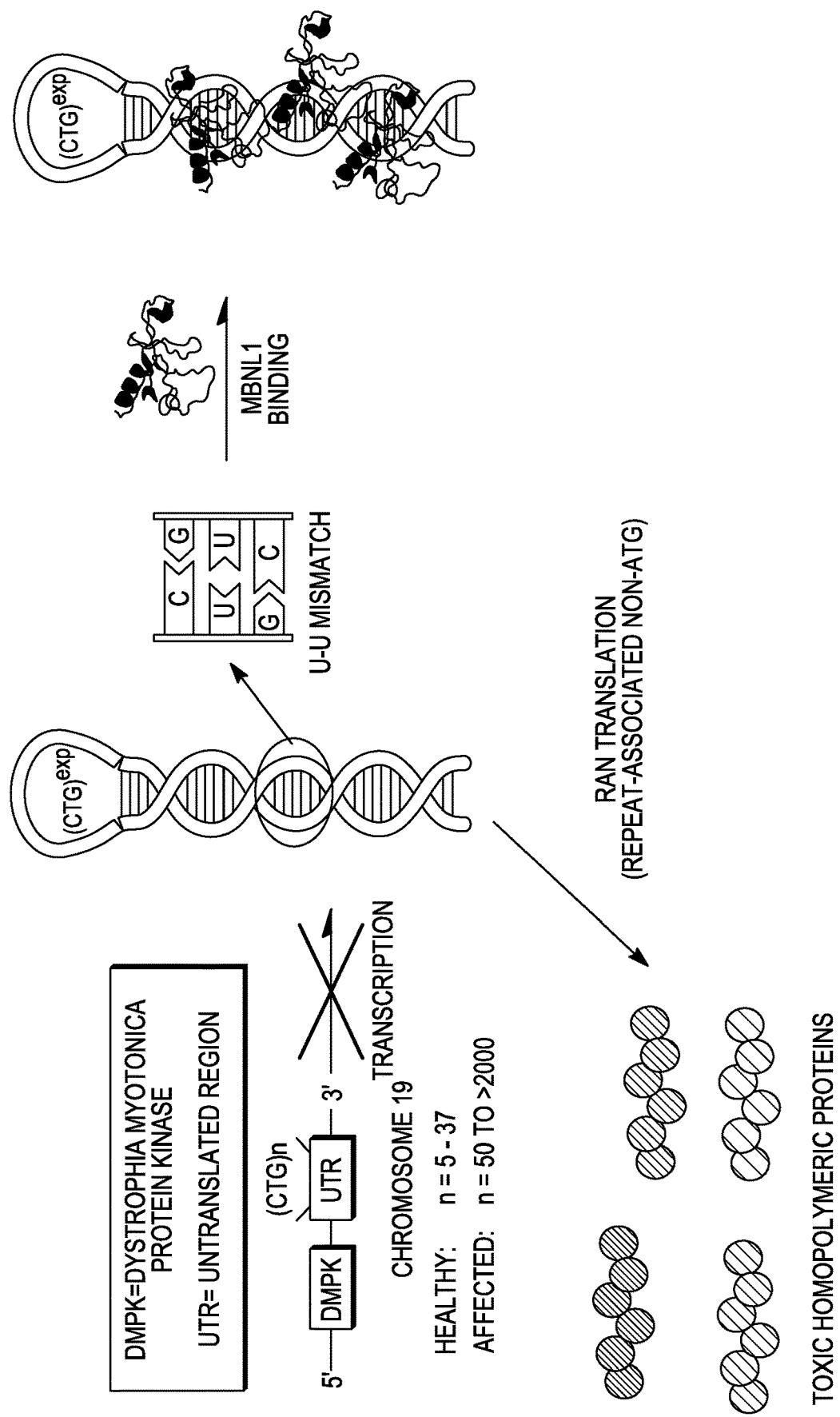
FIG. 10. Pathogenesis of Myotonic Dystrophy type 1.
Figure 11:
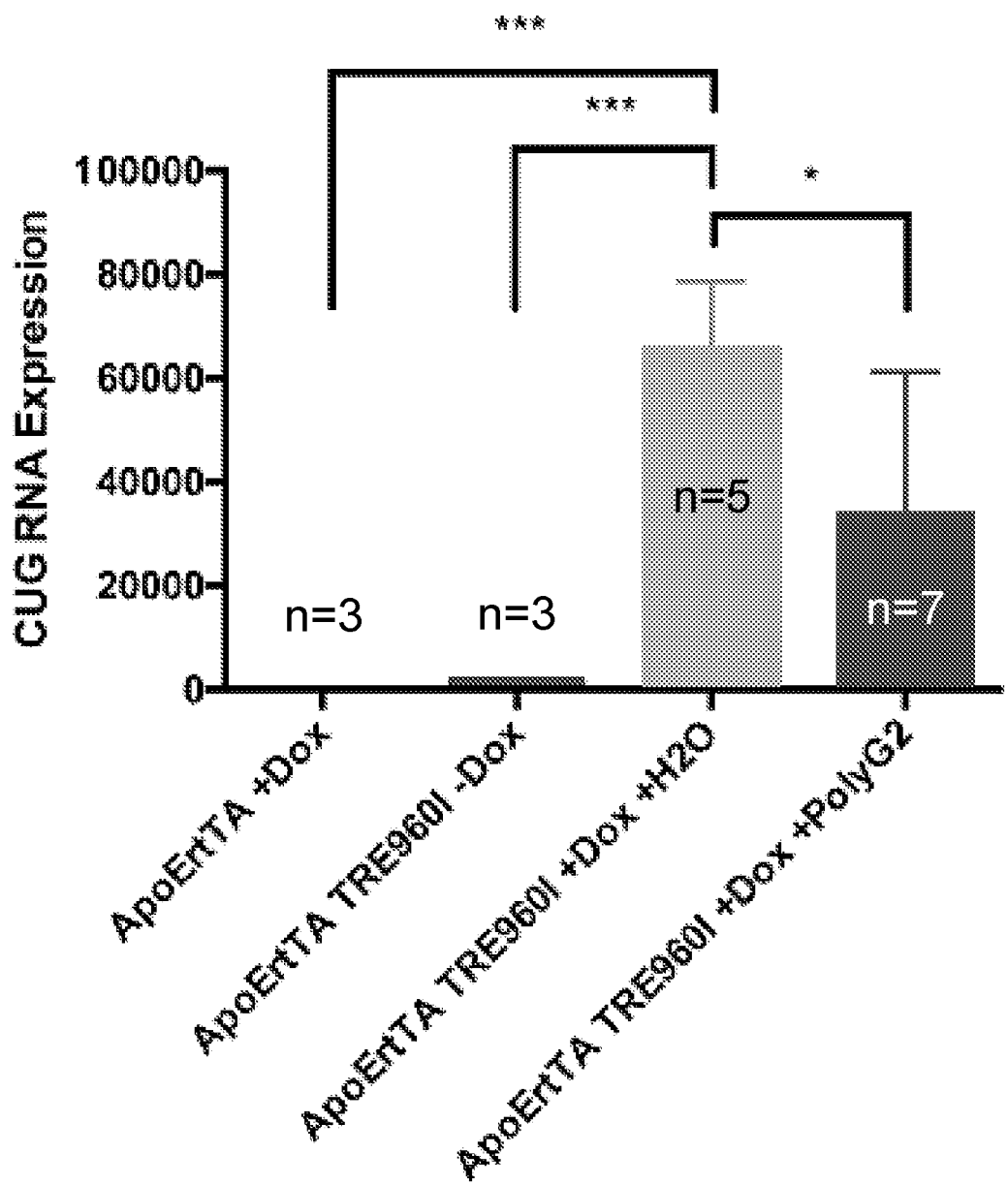
FIG. 11. Repeat RNA levels measured by qPCR. The Butyl-linked Bisamidine/Melamine Oligomer reduces repeat RNA levels in liver model.

In vitro transcription inhibition experiments were performed using (CTG)$^{74}$ containing DNA templates with the presence of 4. In detail, the linearized T7 promoter-containing (CTG)$^{74}$ plasmids were incubated for 3.5 h with T7 polymerase and oligomer 4 of different concentrations ranging from 0 to 400 nM, and the transcription reaction was allowed for 1.5 h. The results of the study were shown in FIG. 7a. A dose dependent effect of 4 on in vitro transcription of (CTG)n-containing DNA template was observed, whereas there was no apparent inhibition on the transcription of non-(CTG)n-containing template by 4. This finding clearly indicates that the oligomer 4 also targets expanded dCTG sequences, possibly by stabilizing its hairpin structure. It is worth noting that the monomeric ligand 1 does not bind to dCTG repeats and gives no transcription inhibition effect in previous studies. The additional substitution on the amino group of the triaminotriazine moieties may have resulted the ligand's elevated affinity towards CTG$^{exp}$, similar to what was observed before for the derivative of 1. With multivalence, 4 achieves full CTGP$^{exp}$ transcription inhibition at much lower concentration compared to the monomeric derivative of 1.

To further examine the potential of 4 in regulating the cellular levels of CUG$^{exp}$, it was studied using the same DM1 model cells in a way similar to previous reports. The model cells were incubated with 4 (0 to 2 µM) for 3 d. The total RNA was isolated and the r(CUG)960 mRNA level was determined by measuring the mRNA levels of exon 15 upstream of CUG$^{exp}$ using PABP mRNA as an internal standard. The results shown in FIG. 7b indicate that the toxic mRNA level was decreased by approximately 20-50% depending on the concentration of 4 used, and the inhibition potency reached a plateau with [4]>200 nM. This study strongly suggests that the oligomer 4 act multifunctionally inside the cells, which likely leads to stronger inhibition of cellular DM1 phenotypes.

Oligomer 4 Rescues the Climbing Defect of Adult Flies in a DM1 Drosophila Model

Recently reported was a peptide-based multivalent ligand which was evaluated in a crawling assay using DM1 transgenic Drosophila larvae models. Preliminary data suggested that 4 also significantly rescue the locomotive defect of the larvae, however, 4 was tested with a more advanced climbing assay using adult Drosophila. As a neurodegenerative disease, DM1 affects the central nervous system and the motor system, which can both be evaluated by the Drosophila adult climbing assay. In addition, DM1 flies showed the age-dependent progressive climbing defects. The adult flies can be aging for several days even for months which cannot be done in larvae. By aging the adult flies, more rCUG$^{exp}$ would have been accumulated, and a model with more severe defects to screen for more powerful inhibitors is obtained. Moreover, the climbing assay allows fast screening using a larger amount of adult flies, generating statistically important data faster and more conveniently.

The principle of the climbing assay is to put certain number of flies in the bottom of a tube, and as an innate behavior, the flies will attempt to climb to the top of the tube, opposed to gravity. And the result scores on the total number of flies climbed past a marked threshold on the tube during an allotted time period. Ligand 1 and 4 were head-to-head compared using the climbing assay and the results were shown in FIG. 7c. For all the Drosophila studies, crosses were set at 21.5° C. F1 flies were cultured at 25° C. and those of 5dpe were used for the assay. The number of flies that climbed higher than a 6 cm threshold in 10 s was scored. For normal flies, treatment of 4 (80 µM) gave no effect in their climbing ability, suggesting minimal toxicity of 4 to the flies, whereas 1 slightly decreased the flies' climbing capability. For disease model flies, almost 80% of the flies failed to climb, but upon treatment of 4 (20-80 µM), their climbing ability was rescued by approximately 50%, to a 37% failure rate at highest dosage. For the monomeric ligand 1, only at 400 µM concentration can the failure rate be dropped to 55%, which clearly showed the effectiveness of the multivalent effect. These results demonstrate the in vivo efficacy of 4 in the DM1 Drosophila larval crawling assay, and suggest that success of this vehicle-free, multivalent design.

Figure 12:
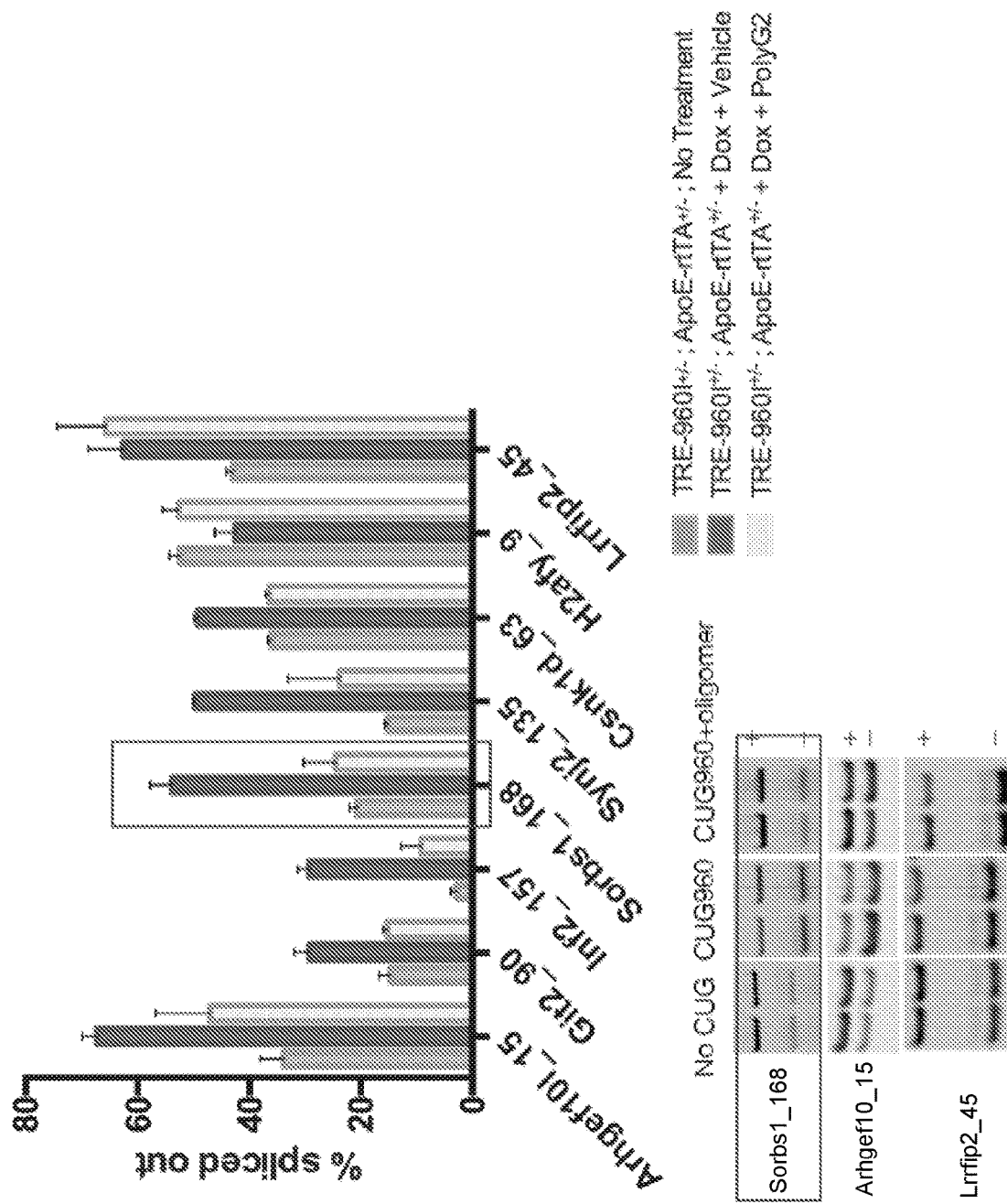
FIG. 12. Splicing Rescue by Oligomer in DM1 Mouse Model.
Figure 13:
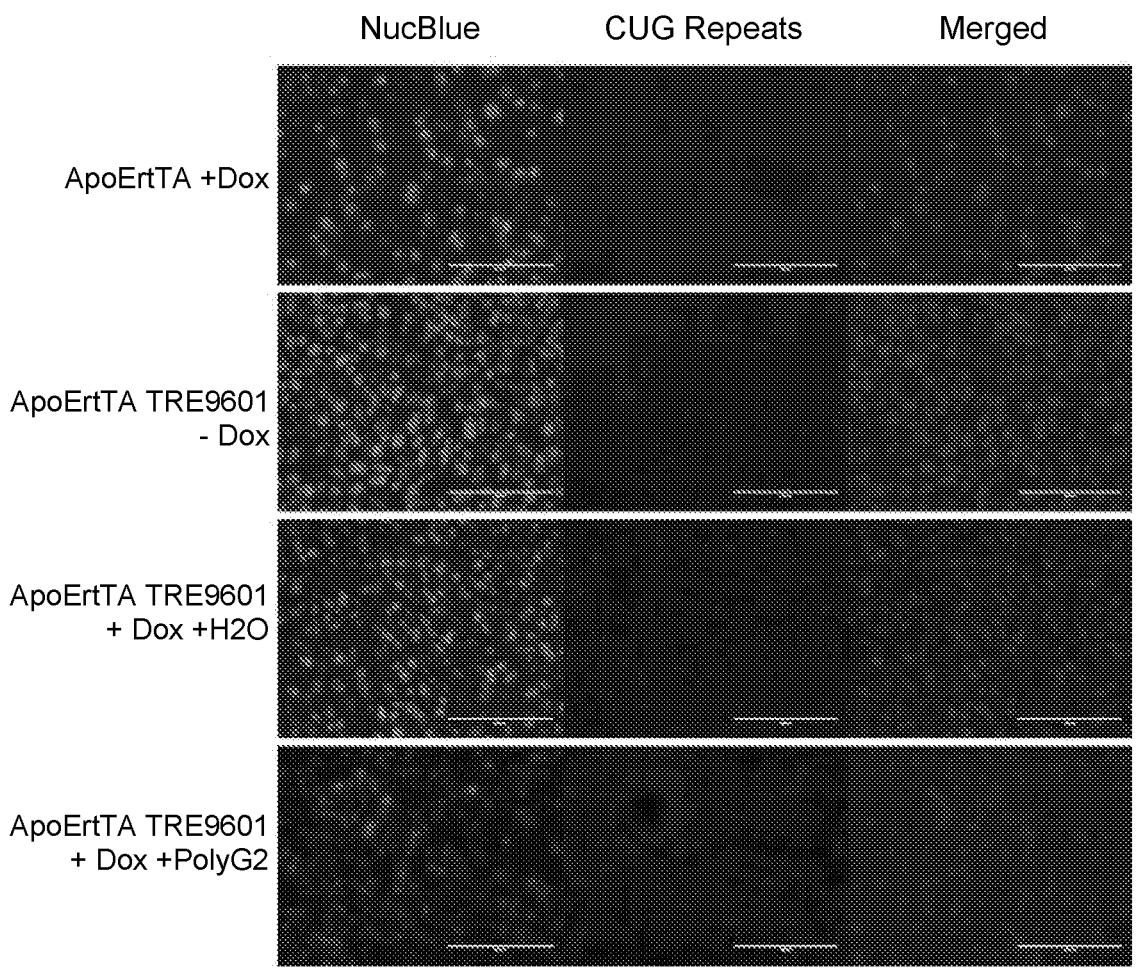
FIG. 13. Nearly full rescue of three splicing defects found in DM1 liver model.

FIG. 12 shows splicing rescue by Oligomer in DM1 mouse model. Most of the MBNL1 regulated splicing defects are nearly fully rescued.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The multivalent compounds (e.g., oligomers) described herein can be effective myotonic dystrophy and have higher potency and/or reduced toxicity as compared to non-multivalent compounds. The invention provides therapeutic methods of treating myotonic dystrophy type 1 (DM1) in a mammal, which involve administering to a mammal having DM1 an effective amount of a compound or composition described herein. A mammal includes a primate, human, rodent, canine, feline, bovine, ovine, equine, swine, caprine, bovine and the like. The ability of a compound of the invention to treat DM1 may be determined by using assays well known to the art.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Procedures

Synthesis of Oligomer 4.

The synthesis of 4 is shown in Scheme 1. Under N$_2$, the two monomer, diethyl terephthalimidate dihydrochloride (DETPI.2HCl, 29.3 mg, 0.1 mmol, 1 eq.) and N2,N4-bis(4-aminobutyl)-2,4,6-triamino-1,3,5-triazine bis-trifluoroacetate (BABTT-2TFA, 49.6 mg, 0.1 mmol, 1 eq.) was mixed in 1 mL of anhydrous DMF in a 7 mL glass vial with a silicone-top screw cap. Triethylamine (TEA, 83.7 µL, 0.6 mmol, 6 eq.) was added, and the reaction was kept at 35° C. with stirring for 96 h. The resulting mixture was added aq. HCl (3.0 M, 2 mL), and the solution was dialyzed against water (MWCO=1 kDa) for 20 h. The purified solution was lyophilized to give a white solid as the product (31 mg).

In Scheme 1, the starting reagent, an aminoalkyltriazine can generally be prepared from a triazine having various leaving groups reacting with an alkyldiamine, for example, 2-amino-4,6-dicholoro-1,3,5-triazine contacting a tetramethylenediamine. The other starting reagent, a phthalimidate, can generally be prepared from a phthalonitrile and an alcohol, or a phthaloyl halide and an amine.

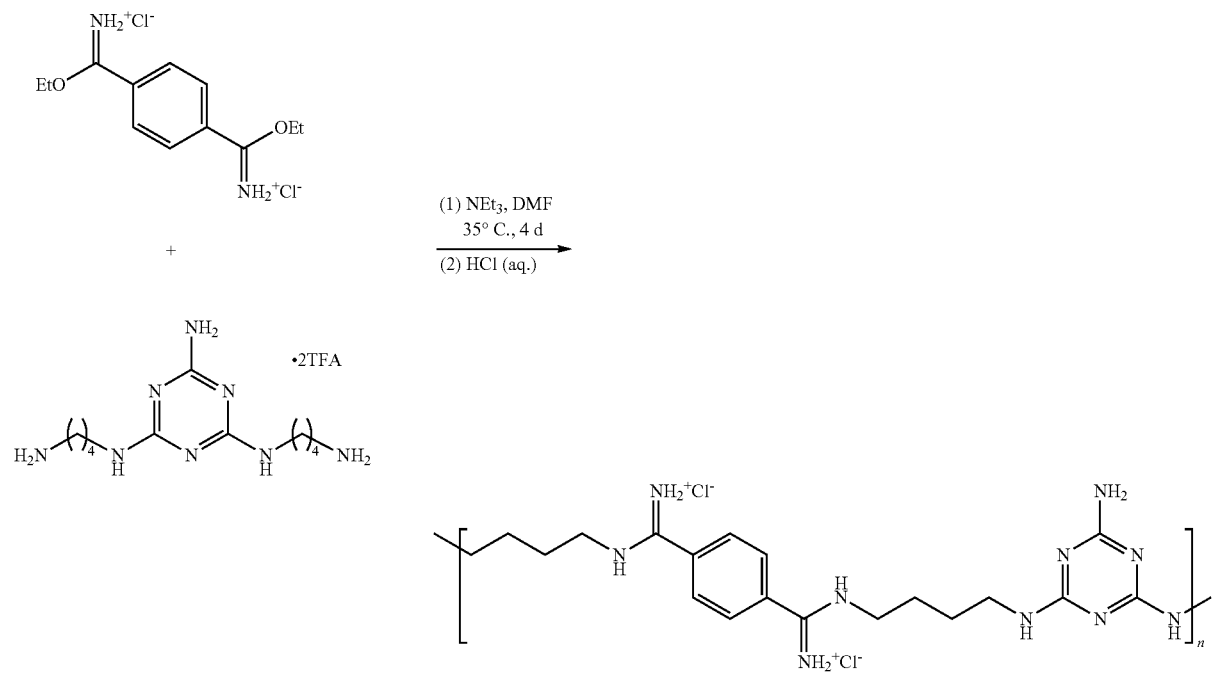

Oligomer Binding with r(CUG).

The ITC experiment was conducted as previously reported with minor changes (*J. Am. Chem. Soc.* 2014, 136, 6355). The concentrations of MOPS, NaCl, r(CUG), and oligomeric ligand 4 were 20, 150, 0.01, 0.5 mM, respectively. For comparison, the binding affinity of 1 was also measured under similar conditions, with the concentration of r(CUG) being changed to 0.02 mM).

Confocal Microscopy.

Cell penetration study and imaging of ribonuclear foci in DT960 transfected HeLa cells were performed as previously described (*ACS Chem. Bio.* 2013, 8, 1037).

mRNA Splicing Assay.

The rescue of the mis-splicing of insulin receptor (IR) pre-mRNA was studied using a previously reported splicing assay (*J. Am. Chem. Soc.* 2014, 136, 6355—see supplemental information).

Drug Treatment in *Drosophila*.

*Drosophila* lines were cultured in standard cornmeal medium supplemented with dry yeast. Fly lines bearing UAS-(CTG)$_{60}$ and UAS-(CTG)$_{480}$ were kind gifts of Prof Rubén Artero Allepuz (Universitat de València, Estudi General, Spain). The elav-GAL4 fly line was obtained from Bloomington *Drosophila* Stock Center. Ligand 1 and Ligand 4 were dissolved in ddH$_2$O and mixed with fly food. Genetic crosses were set up in normal or drug-containing fly food at 21.5° C. Adult F1 flies were cultured in normal or drug-containing fly food at 25° C. for 5 days and then used for climbing assay.

Adult *Drosophila* Climbing Assay.

This assay was performed as described previously (*Nature* 2000, 404, 394). Groups of 10 flies were anesthetized and placed in a 15 mL vertical tube. The flies were allowed to recover for 1 hour and then were banged to the bottom of the tube. The total number of flies climbed higher than a 6 cm threshold in 10 s was scored. Three trials were repeated in 5 min intervals for each experimental group. Forty flies were tested per treatment group for each set of experiment. The experiments were repeated independently for three times using adult F1 collected from separate genetic crosses.

Example 2. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |

-continued

| (ix) Topical Ointment | wt. % |
|---|---|
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A multivalent ligand represented by Formula I:

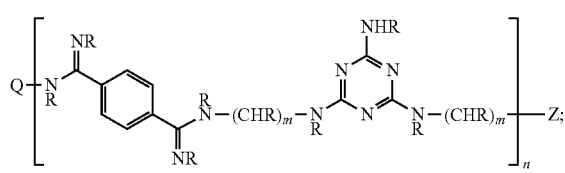

or a salt thereof;

wherein
Q is $-(CHR)_n G^1$ wherein n is 2-5, $G^1$ is

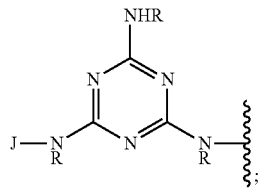

J is $-(CHR)_n-G^2$ wherein n is 2-5;
$G^2$ is OR, $NR_2$, or

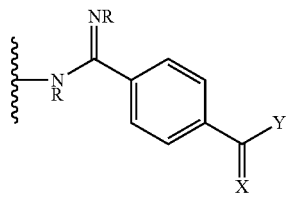

wherein X is O or NR, and Y is OR or $NR_2$;
Z is OR, $NR_2$, or

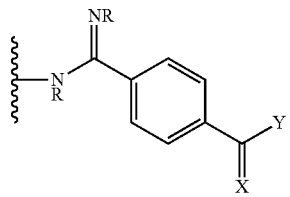

wherein X is O or NR, and Y is OR or $NR_2$;
each R is independently H or branched or unbranched $-(C_1-C_6)$alkyl;
m is 2-8; and
n of Formula I is 2-20.

2. The multivalent ligand of claim 1 wherein R is H.

3. The multivalent ligand of claim 1 wherein m is 4.

4. The multivalent ligand of claim 1 wherein the molecular weight of the multivalent ligand is about 0.5 kDa to about 10 kDa, and the multivalent ligand is cell permeable.

5. The multivalent ligand of claim 1 wherein the multivalent ligand selectively binds to rCUG(exp).

6. The multivalent ligand of claim 5 wherein the multivalent ligand has a binding affinity (Ki) of about 1 nanomolar to about 10 micromolar.

7. The multivalent ligand of claim 1 wherein the multivalent ligand inhibits transcription of CTG(exp).

8. A pharmaceutical composition comprising the multivalent ligand according to claim 1 in combination with a pharmaceutically acceptable diluent, carrier, excipient, or buffer.

9. A method of relieving a sequestered muscleblind-like 1 (MBNL1) protein, comprising contacting a sequestered MBNL1 protein with a multivalent ligand according to claim 1, thereby relieving the sequestered MBNL1 protein, wherein the sequestered MBNL1 protein is sequestered by rCUG(exp).

10. The method of claim 9 wherein the multivalent ligand selectively binds to one or more CUG moieties of rCUG (exp).

11. The method of claim 9 wherein contacting a sequestered MBNL1 protein with a multivalent ligand is in a cell afflicted with myotonic dystrophy type 1 (DM1), and the area of a focal inclusion in the nucleus of the cell is reduced compared to the area of a focal inclusion in the nucleus of a second cell afflicted with DM1, when a sequestered MBNL1 protein is not in contact with the multivalent ligand in the second cell.

12. A method of reducing the symptoms of myotonic dystrophy type 1 (DM1) comprising administering to a subject having DM1 an effective amount of a multivalent ligand according to claim 1, thereby reducing the symptoms of DM1.

13. The method of claim 12 wherein the symptoms of DM1 reduced by the administration are one or more of myopathy, myotonia, progressive muscle atrophy, cataracts, cardiac defect, and insulin dependent diabetes.

14. The method of claim 12 wherein the effective amount is a concentration of about 0.1 micromolar to about 10 micromolar.

15. A method of preparing a multivalent ligand according to claim 1 comprising:
a) contacting a mixture of a dialkyl terephthalimidate and an (aminoalkyl)triaminotriazine to form a product; and
b) acidifying the product;
wherein the acidified product provides the multivalent ligand according to claim 1.

16. The method of claim 15 further comprising dialyzing the acidified product to form a purified product.

17. The multivalent ligand of claim 1 wherein the multivalent ligand is represented by Formula II, III, or IV

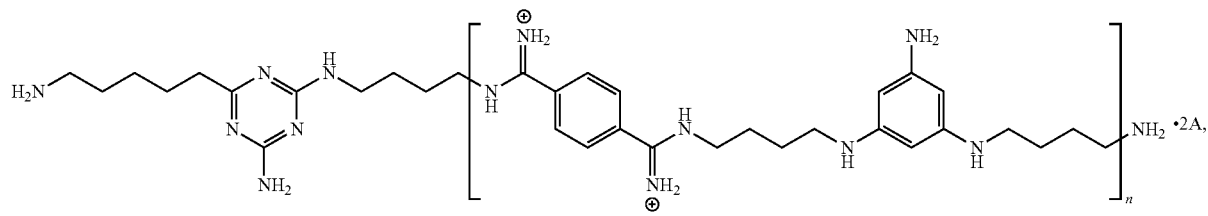

(II)

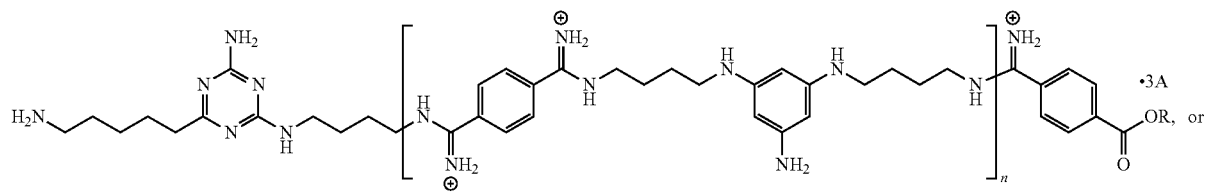

(III)

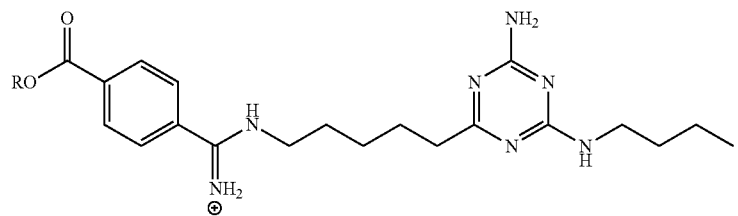

(IV)

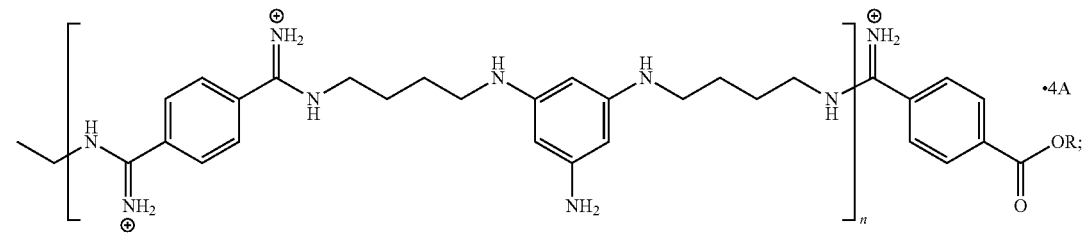

wherein
R is H or ethyl;
n is 2-20; and
A is Cl$^-$, Br$^-$, I$^-$, TFA$^-$, HSO$_4^-$, AcO$^-$, HCO$_3^-$, TsO$^-$, MsO$^-$, or PhSO$_3^-$.

18. The multivalent ligand of claim 17 wherein n is about 4-8.

* * * * *